(12) United States Patent
Piras et al.

(10) Patent No.: US 6,639,104 B2
(45) Date of Patent: Oct. 28, 2003

(54) PROCESS FOR THE RECOVERY OF PURIFIED TEREPHTHALIC ACID (PTA)

(75) Inventors: Luciano Piras, Milan (IT); Michelle Chiarelli, Landriano (IT); Sergio Schena, Mantova (IT); Luigi Soro, Ghilarza (IT)

(73) Assignee: Inca International S.p.A., Milan (IT)

( * ) Notice: Subject to any disclaimer, the term of this patent is extended or adjusted under 35 U.S.C. 154(b) by 0 days.

(21) Appl. No.: 10/168,227

(22) PCT Filed: Nov. 30, 2000

(86) PCT No.: PCT/IB00/01898

§ 371 (c)(1),
(2), (4) Date: Jun. 18, 2002

(87) PCT Pub. No.: WO00/71226

PCT Pub. Date: Nov. 30, 2000

(65) Prior Publication Data

US 2003/0004373 A1 Jan. 2, 2003

Related U.S. Application Data

(60) Provisional application No. 60/170,293, filed on Dec. 10, 1999.

(51) Int. Cl.[7] .............................................. C07C 51/42
(52) U.S. Cl. ..................... 562/494; 562/485; 562/486
(58) Field of Search ................................. 562/485, 486, 562/474

(56) References Cited

U.S. PATENT DOCUMENTS 3,584,039 A * 6/1971 Meyer ........................ 562/416
3,799,976 A * 3/1974 Nienburg et al. ........... 562/416
4,438,279 A * 3/1984 Packer et al. ................ 562/416
4,467,111 A * 8/1984 Puskas et al. ................ 562/487
5,110,984 A * 5/1992 Janulis ........................ 562/487
5,175,355 A * 12/1992 Streich et al. ............... 562/485

FOREIGN PATENT DOCUMENTS

WO        WO 00/71226        11/2000

* cited by examiner

*Primary Examiner*—Alan L. Rotman
*Assistant Examiner*—Taylor V Oh

(57) ABSTRACT

A process for the preparation of purified terephthalic acid which comprises first introducing a liquid slurry containing crystalized terephthalic acid with impurities into a high pressure rotary filter, then filtering the slurry with the high pressure rotary filter and collecting at least some of the solid portion. The filter typically consists of a case, pressurized at process pressure, and a drum covered by a filtering device such as, for example, a cloth or equivalent filtering device, pressurized at a pressure suitably lower than the case. The drum is ideally divided into three zones: first zone, where the mother liquor is removed; second zone, where the solid is washed; third zone, where the excess of washing liquor is removed and the solid is discharged. The solid portion is washed, onto the filter drum, with additional amounts of water. The washed solid portion is then transferred to a letdown zone, which is at a pressure less than the zone in which the solid portion was collected. After the solid portion is transferred into the letdown zone, the connection between the letdown zone and the collection zone is sealed, such that a change of pressure in the letdown zone will not effect the pressure in the collection zone. The pressure of the letdown zone is then gradually reduced and the solid removed. The letdown zone is then pressurized back up so that it is ready to accept additional solid from the rotary filter.

5 Claims, No Drawings

PROCESS FOR THE RECOVERY OF PURIFIED TEREPHTHALIC ACID (PTA)

This application claims the benefit of provisional application 60/170,293 filed Dec. 10, 1999.

The present invention relates to a new process for the production and recovery of purified terephthalic acid ("PTA"). More particularly, this application relates to the use of a rotary pressure filter to recover crystalline terephthalic acid and a process to recover the resulting crystals at atmospheric pressure. The process involves moving the crystalline material through at least two valves defining separate zones, wherein each succeeding zone is at a pressure slightly less than the previous zone.

Terephthalic acid is used in the production of many different polymers, including polyethylene terephthalate (PET). The typical process for PET is the direct condensation of terephthalic acid with a polyalcohol. This direct esterification reaction requires purified terephthalic acid, for the reaction product to be acceptable.

Terephthalic Acid is produced by direct oxidation of p-xylene and subsequent crystallization from the mother liquor to recover the Crude Terephthalic Acid (CTA). This CTA still contains approximately 0.2–0.4% by weight of 4-carboxybenzaldehyde (4-CBA) as major impurity. To reduce the content of 4-CBA, the CTA is typically dissolved in water and then the resulting solution is treated in a hydrogenation reactor, to convert the 4-CBA into p-toluic acid. The solution from the hydrogenation reactor is then typically cooled by flash in a battery of crystallizers to precipitate the purified terephthalic acid (PTA) as a crystal. The slurry coming from the crystallizers still contains a significant amount of p-toluic acid that needs to be separated from PTA, to meet the usual commercial specification of no more that 150 ppm.

In order to purify the PTA two subsequent stages of solid separation are most currently used. The traditional method to separate the PTA from its mother liquor consists in centrifuging the slurry at a temperature of from 100° C. to 170° C. and a pressure of from 1 to 7 bar. Under these conditions the majority of the p-toluic acid will remain in solution, allowing it to be separated.

The crystals of PTA coming from the centrifuges contain only a small amount of p-toluic acid, but do contain residual mother liquor (typically 10–15%). To get rid of these impurities, the crystals are usually mixed with additional water, typically in a ratio of 1.1 to 1.5 $m^3$ water/ton PTA, to wash the mother liquor still entrained. This results in a slurry having a 45±5% solids. This slurry is then flashed to atmospheric pressure and fed either to a second stage of centrifuges or to Rotary Vacuum Filters (RVF). The PTA, containing a residual 10–15% of water, is then dried, typically in a rotary dryer, and stored. The PTA crystals still contain minor amounts of p-toluic acid (usually less than 150 ppm) while 4-CBA content is typically lower than 25 ppm.

These traditional methods have high capital costs in that they require a large scale pressure centrifuge as well as either a large scale RVF or a second large scale centrifuge. This in turn leads to high maintenance costs with accompanying lack of reliability. Additionally the centrifuge causes significant crystal breakage such that the particle size distribution is greatly enlarged, especially of particle sizes less than 44 microns. This process also requires a lot of water that needs to be heated up to the process temperature. Finally the process results in a product with a relatively large amount of moisture which must be removed in the dryer, resulting in high energy consumption.

U.S. Pat. No. 5,175,355 teaches a method of purifying the terephthalic acid comprising pressure filtering. This reference teaches introducing an aqueous slurry (comprising purified terephthalic acid present as crystals and p-toluic acid present in the aqueous solution and as a co-crystallized form) into one or more filter cells. The slurry is filtered at a system pressure of from atmosphere to 16 atm. The filter cell with the resulting filter cake is then transported into a wash zone where a stream of water heated to 38° C. to 205° C. is introduced to the filter cell to form a reservoir of water over the filter cake. Displacement washing is then achieved by forcing the water through the cake at a pressure gradient, which is at least 0.5 atm above the system pressure while maintaining the reservoir. The displacement washing is allowed to continue for a sufficient time to remove a desired amount of impurities. The filter cell is then transported to a pressure release zone wherein the system pressure is quickly released to flash evaporate the water remaining in the filter cake and the product is recovered. The pressure release zone is then pressurized back up to the system pressure so as to be ready to accept additional product. This process reportedly results in terephthalic acid that contains less than 200 ppm by weight of p-toluic acid.

While this process satisfactorily produces pure product, it is a time consuming process as the pressure release zone repeatedly has to be pressurized back up to the system pressure before it can accept more displacement washed material.

The applicants of the present invention have found that the process can be improved by transferring the washed filter cake to a letdown zone (or pressure release zone) which is at a pressure less than the pressure of the washing zone. In this way the time required to pressure up the letdown zone is dramatically reduced. The applicants of the present invention have discovered that the pressure of the letdown zone approaches the desired pressure asymptotically. That is to say that the majority of the pressure differential between the release pressure and the system pressure is made up in the early stages of re-pressurization, whereas the final bit takes a relatively longer period of time. Thus, by allowing the letdown zone to be pressurized to a pressure less than the system pressure, much time can be saved. Shortening the cycle time allows the front end of the production to be run faster, or alternatively allows smaller rotary pressure filters to be used without causing a bottleneck.

Furthermore, it has been discovered that a pressure differential between the letdown zone and the washing zone actually facilitates the movement of product, as it is carried to some extent by the flow of gas, which occurs when the barrier between the two zones is removed. This also has been observed to help keep the filter itself free from clogging.

Additionally the applicants of the present invention have discovered that it is advantageous, for the best mechanical performance of the system mainly to avoid plugging of the vent line, to release the pressure more slowly than the flash evaporation taught by U.S. Pat. No. 5,175,355.

One aspect of the invention is a process for the preparation of purified terephthalic acid which comprises first introducing a liquid slurry containing crystallized terephthalic acid with impurities into a high pressure rotary filter, then filtering the slurry with the high-pressure rotary filter and collecting at least some of the solid portion. Then the solid portion is washed with additional amounts of water. The washed solid portion is then transferred to a letdown zone, which is at a pressure less than the zone in which the solid portion was collected. After the solid portion is transferred into the letdown zone, the connection between the letdown zone and the collection zone is sealed, such that a change of pressure in the letdown zone will not effect the pressure in the collection zone. The pressure of the letdown zone is then reduced and the solid removed. The letdown zone is then pressured back up so that it is ready to accept additional solid from the rotary filter.

The liquid slurry containing the terephthalic acid containing the impurities can come from any terephthalic acid production scheme. These are known in the art and are of minimal importance to the invention at hand. The particular high-pressure rotary filter used to filter the slurry is similarly not critical to the present invention. Any filtering system capable of operating at a pressure greater than atmospheric pressure may be used. Preferably, for standard operating conditions, the filter is capable of handling the full throughput of terephthalic acid of the plant, and capable of operating under pressures of from 1.0 to 10.0 bar. A suitable filter is the Bird Young Rotary Filter sold by Baker Process Inc. The filter used in the apparatus of the present invention was a Bird Young Rotary Filter having a filtration area of 1 sq. ft and was able to process from 1 to 5 MT/h of solid PTA.

The filter typically consists of a case, pressurized at process pressure, and a drum covered by a filtering device such as a cloth or equivalent filtering device, pressurized at a pressure suitably lower than the case.

The drum is ideally divided into three zones:

First zone, where the mother liquor is removed.

Second zone, where the solid is washed.

Third zone, where the excess of washing liquor is removed and the solid is discharged.

The pressure of the case is preferably in a range of from 3 to 6.5 bar, with about 4.5 bar being most preferred. The filtering is carried out at a temperature of from 133° C. to 161° C., with 147° C. being most preferred.

The pressure difference between case and drum is in the range of 0.1 to 2.0 bar, preferably in the range of 0.3 to 0.7 bar, most preferably 0.5 bar.

The mother liquor removed from the rotary pressure filter can be separately recovered and reused into the production process or sent to waste treatment facilities, as is known in the art.

The remaining solid portion is then washed with additional amounts of water. It has been discovered that less wash water is required in the present process to achieve purity similar to the traditional methods. Thus while any amount of water may be used in the washing stage of the present invention, it is preferred that less than 1 cubic meter per ton of PTA be used, in order to conserve water and reduce the energy associated to heating up this water to process temperature. The water amount is preferably in a range of from 0.2 to 0.7 m$^3$/MT of PTA, with about 0.5 m$^3$/MT of PTA being most preferred. The washing is preferably done at the same temperature as the filtering, although this is for convenience and is not mandatory. The temperature of the water used to wash the solid material is in the range of 50° C. to 161° C., preferably in the range of 130° C. to 150° C., most preferably 147° C. The wash liquor can then be separately collected from the mother liquor and reused into the production process or recycled back into the production process, as is known in the art.

After washing, the solid material is preferably collected in a collection zone and then passed into a let down zone, which is at a pressure that is less than the collection zone. To maintain the pressure difference the collection zone is preferably separated from the letdown zone by a device of some sort, which can readily open and close to seal the letdown zone from the collection zone. Thus in operation, when an amount of solid material had collected in the collection zone, the device would be opened and the combination of gravity and the pressure differential would cause some (preferably all) of the solid material to move to the letdown zone. The device is not critical to the invention, however hemispheric valves (Dome Valves) such as those manufactured by Macawber Engineering Inc., have been shown to be effective.

When the device is opened the letdown zone is at a pressure that is somewhat less than the collection zone. Preferably this pressure difference is in the range of 0.01 to 0.3 bar, preferably in the range of 0.03 to 0.1 bar, most preferably 0.05 bar.

After the solid has moved into the letdown zone the device is closed, sealing off the letdown zone from the collection zone and/or rotary pressure filter. At this time the pressure is released. While flash evaporation can be used with the invention, it is preferred that the pressure be released more slowly. Ideally the pressure is released over a period from 0.5 to 10 seconds, more preferably from 4 to 7 seconds, although the optimal time will be a factor of the individual machinery and how fast the train is running. The slow release of pressure can be achieved by many different methods. One way is just to have a narrow restriction in the vent line, which can be controlled. This can be used alone or in conjunction with a check valve, which maintains a certain pressure in the line (and therefore the letdown zone). Other methods such as bleed valves are well known in the art and can be used with the present invention. A second vent line without any restrictions can also be used as a double check to ensure that the letdown zone does not remain pressurized.

Once the letdown zone has been depressurized a second sealing device is opened and the solid contents are removed As in the transition from the collection zone to the letdown zone, this transition is preferably conducted with a slight pressure differential so that when the sealing device is opened the contents are carried by gravity as well as the flow of gasses into the region of lesser pressure. Preferably this pressure difference is in the range of 0.01 to 0.3 bar, preferably in the range of 0.03 to 0.1 bar, most preferably 0.05 bar. Again any device capable of sealing the letdown zone can be used, however the Dome Valves are preferred. The solid material can then be passed to a drier by mean of suitable device, such as a screw, for further processing as is known in the art.

When the contents have been removed from the letdown zone, the letdown zone is once again sealed off with the Dome Valve (or other suitable means) and then the letdown zone is pressured back up to a pressure suitable to accept more washed material. Preferably, the time it takes to release the pressure in the letdown zone, remove the product, and re-pressurize the letdown zone is calculated to correspond to the time it takes to fill up the collection zone, so that as soon as the letdown zone is emptied, sealed and re-pressurized, the collection zone is full, so that there is no down time in the cycle. As stated before, by not requiring the letdown zone to be at the same pressure as the collection zone (or rotary pressure filter case), the letdown zone can be pressurized up to acceptable limits much more quickly. Thus the process can begin again almost immediately.

Preferably, a Programmable Logic Controller (PLC) is used to run the sequence above described, in order to optimize the opening and closing of the various sealing devices, venting devices, and pressurization lines.

EXAMPLES

Example No. 1

Various tests have been performed to investigate the quality results versus different operating conditions. This example describes only tests performed keeping constant the pressure differential (dp) between the case and the drum to a value of 0.55 bar.

A description of the operating values is reported in table 1.

A description of the quality results is summarized in table 2.

TABLE 1

| Operating conditions | Pressure filter | Two stages of centrifuges |
|---|---|---|
| Case pressure | 4.3 bar | 3.8 bar |
| Dp casing/drum | 0.55 bar | — |
| Washing water | 200–500 kg/TPTA | — |
| Reslurry water | — | 1100 kg/ TPTA |
| Depressurization time (1) | 1–10 sec. | — |
| Differential pressure (2) Between zones | 0.01–0.05 bar | — |

TABLE 2

| Product quality | Pressure filter | Two stages of centrifuges |
|---|---|---|
| Other by products | 90–230 ppm | 120–240 ppm |
| P-toluic acid | 50–140 ppm | 20–140 ppm |
| Humidity | 8–10% | 10–15% |

(1) Time of depressurization of the letdown chamber.
(2) Differential pressure between the accumulation chamber and let down chamber and between the let down chamber and the final discharge line at atmospheric pressure.

What is claimed is:

1. A process for the preparation of purified terephthalic acid which comprises:

a. introducing a liquid slurry containing crystallized terephthalic acid with impurities into a high pressure rotary filter;
   b. filtering said slurry and collecting at least some of the solid portion;
   c. washing the solid portion with additional amounts of water and collecting the washed solid portion in a collection zone under pressure of from 1.0 to 10.0 bar;
   d. passing the collected washed solid portion from the collection zone to a letdown zone, wherein the letdown zone is at a pressure at least 0.01 bar less than the collection zone;
   e. sealing a connection between the letdown zone and the collection zone, such that a change of pressure in the letdown zone will not effect the pressure in the collection zone;
   f. reducing the pressure of the letdown zone;
   g. removing the washed solid portion from the letdown zone; and
   h. increasing the pressure of the letdown zone to 0.01 to 0.3 bar less than the pressure of the collection zone so that it may accept additional washed solid material from the high pressure rotary filter.

2. The process of claim 1, wherein the pressure is released in step f over a period of more than 10 seconds.

3. The process of claim 1, wherein the temperature of the wash is from 50° C. to 161° C.

4. The process of claim 1 wherein the solid portion is washed at a rate of less than 1.1 cubic meters of water per ton of solid.

5. The process of claim 1 wherein the pressure of the letdown zone is not reduced to atmospheric pressure such that there is a pressure differential to help in the removal of the product.

* * * * *